United States Patent
Uno et al.

(10) Patent No.: US 7,125,575 B2
(45) Date of Patent: *Oct. 24, 2006

(54) METHOD OF REMOVING OFF-FLAVOR FROM FOODS AND DEODORIZER

(75) Inventors: Kazutaka Uno, Tsuchiura (JP); Chiaki Saitoh, Inashiki (JP); Makoto Egi, Tokyo (JP); Shoji Ago, Kitakyushu (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/837,784

(22) Filed: May 4, 2004

(65) Prior Publication Data

US 2004/0202748 A1    Oct. 14, 2004

Related U.S. Application Data

(62) Division of application No. 09/826,954, filed on Apr. 6, 2001, now Pat. No. 6,893,669.

(30) Foreign Application Priority Data

Apr. 6, 2000   (JP) .............................. 2000-104277

(51) Int. Cl.
*C12C 3/12* (2006.01)
*A23L 1/22* (2006.01)

(52) U.S. Cl. .............................. 426/18; 426/7; 426/28; 426/29; 426/30; 426/534; 426/541; 426/590

(58) Field of Classification Search .................. 426/7, 426/11, 12, 13, 18, 28, 29, 30, 534, 541, 590, 426/592

See application file for complete search history.

(56) References Cited

U.S. PATENT DOCUMENTS 4,358,462 A    11/1982   Takeda 6,022,576 A    2/2000   Cirigliano et al.
6,048,560 A    4/2000   van Dort et al.
6,265,000 B1   7/2001   Shimamura et al.
6,893,669 B1*  5/2005   Uno et al. .................... 426/18

FOREIGN PATENT DOCUMENTS

| EP | 0 574 941 A2 | 12/1993 |
| WO | 96/22702 * | 8/1996 |
| WO | WO 96/22702 | 8/1996 |
| WO | WO 00/47045 | 8/2000 |

OTHER PUBLICATIONS

Abstract of JP 62208264 (Sep. 1987).
Abstract of JP 60087782 (May 1985).
Abstract of JP 57094286 (Jun. 1982).
Abstract of JP 11313665 (Nov. 1999).
European Search Report for EP 01 10 7465, completed Jan. 25, 2002.
Abstract of JP-356117790A, (Sep. 1981).
Abstract of JP-360186273A (Sep. 1985).
Abstract of JP-362061575A (Mar. 1987).
European Search Report, for Application No. 05021292.7-2114, dated Nov. 18, 2005.

* cited by examiner

*Primary Examiner*—Leslie Wong
(74) *Attorney, Agent, or Firm*—Antonelli, Terry, Stout and Kraus, LLP.

(57) ABSTRACT

The present invention provides an effective method of removing off-flavor from foods such as seafood, meat products and vegetables, which comprises causing a polymer of phenol compounds having a styrene structure and/or a reaction mixture produced by conducting an oxidation reaction of the phenol compounds having a styrene structure in the presence of oxygen to be present in the food. Also provided is a deodorizer comprising a polymer of phenol compounds having a styrene structure.

30 Claims, No Drawings

METHOD OF REMOVING OFF-FLAVOR FROM FOODS AND DEODORIZER

This application is a Divisional application of prior application Ser. No. 09/826,954, filed Apr. 6, 2001, now U.S. Pat. No. 6,893,669 B2, the content of which are incorporated herein by reference in their entirety.

BACKGROUND OF THE INVENTION

The present invention relates to a method of removing off-flavor from foods such as seafood, meat products and vegetables, a deodorizer, and the like.

Among the factors undesirably influencing the quality of food are so-called off-flavors, e.g., the fishy smell of seafood, the fleshy smell of meat, and the grassy smell of soybean. It is known to use sake, wine, shochu, mirin (a sweet sake used as seasoning), etc. in processing or cooking food for the purpose of masking such off-flavors. The deodorizing effect of such substances is considered to be mostly attributable to ethanol.

In addition to ethanol mentioned above, the following substances are known to be effective for deodorization: amino acids and organic acids [J. Jap. Soc. for Food Science and Technology, 29(6), 340 (1982)], amino-carbonyl reaction products [J. Fish Sausage, 212, 15 (1982)], saccharides [J. Jap. Soc. for Food Science and Technology, 46(5), 319 (1999)] and phenol compounds [J. Jap. Soc. for Food Science and Technology, 29(7), 426 (1982)].

Smoking is known as one of the conventional methods of deodorization utilizing food processing techniques. It is reported that the above-mentioned phenol compounds are concerned in the deodorization by smoking [Bull. of the Jap. Soc. of Scientific Fisheries, 47 (1), 113(1981); J. Fish Sausage, 212, 15 (1982)].

Vanillin, which is a kind of phenol compound, is well known as a substance that overcomes the odor of trimethylamine, off-flavor in seafood. However, the characteristic sweet smell of vanillin is regarded as an undesirable odor in certain kinds of foods and thus prevents the utilization of vanillin as a deodorizer.

4-Vinylguaiacol, which is a kind of phenol compound, is a precursor of vanillin. In the field of brewing of sake, wine, etc., 4-vinylguaiacol itself is considered to be one of the off-flavor components, and studies are made to minimize its formation in the process for producing such brewage.

On the other hand, certain yeast and mold are known as enzyme source of ferulic acid decarboxylase having the activity to form 4-vinylguaiacol from ferulic acid, and the ferulic acid decarboxylase gene of yeast has been obtained [Gene, 142, 107 (1994); Japanese Published Unexamined Patent Application No. 276788/98].

SUMMARY OF THE INVENTION

Some of the off-flavors of foods are inherent in food materials, and others are developed in the course of processing or cooking foods. A known example of the latter is the one developed by oxidation of lipid caused by heating. As the off-flavor developed by oxidation can be reduced by suppressing oxidation, it is considered as one of the effective methods for removing off-flavor to cause a substance having antioxidant activity to be present in the system.

An object of the present invention is to provide an effective method of removing off-flavor from foods such as seafood, meat products and vegetables, and to provide deodorizers, etc.

Another object of the present invention is to provide products containing deodorizers of the present invention.

One of other object of the present invention is to provide a method of producing a deodorizer comprising an oxidation reaction step for conducting an oxidation reaction of a polymer of phenol compounds having a styrene structure in the presence of oxygen, and a deodorizer produced by the method thereof.

One of other object of the present invention is to provide a method of producing a seasoning comprising an oxidation reaction step for conducting an oxidation reaction of a polymer of phenol compounds having a styrene structure in the presence of oxygen, and a seasoning produced by the method thereof.

One of other object of the present invention is to provide a method of producing liquor comprising an oxidation reaction step for conducting an oxidation reaction of the resultant liquid of the separation step in the presence of oxygen, and liquor produced by the method thereof.

In one embodiment, the present invention provides a method of removing off-flavor from a food which comprises causing a polymer of phenol compounds having a styrene structure to be present in the food.

In another embodiment, the invention provides a deodorizer comprising a polymer of phenol compounds having a styrene structure.

In another embodiment, the invention provides a seasoning comprising a polymer of phenol compounds having a styrene structure.

In another embodiment, the invention provides a cosmetic comprising a polymer of phenol compounds having a styrene structure.

In another embodiment, the invention provides an antioxidant comprising a polymer of phenol compounds having a styrene structure.

In another embodiment, the invention provides a method of producing a polymer of phenol compounds having a styrene structure, which comprises converting phenol compounds having a styrene structure into the polymer in the presence of oxygen.

In another embodiment, the invention provides a method of producing a seasoning comprising a polymer of phenol compounds having a styrene structure, which comprises causing phenol compounds having a styrene structure to be present in any of the steps in a process for producing a seasoning, and conducting an oxidation reaction of the phenol compounds in the presence of oxygen during or after the completion of the process.

In another embodiment, the invention provides a method of producing a deodorized food, which comprises cooking a food using the above deodorizer.

In another embodiment, the invention provides a method of deodorizing a food, which comprises cooking the food using the above deodorizer.

In another embodiment, the invention provides a method of producing liquor, which comprises an oxidation reaction step for conducting an oxidation reaction of the resultant liquid of the separation step in the presence of oxygen.

DETAILED DESCRIPTION OF THE INVENTION

The phenol compounds having a styrene structure may be any compounds having hydroxy and vinyl on a benzene ring (said vinyl may be substituted by carboxy or the like). Preferred are compounds represented by general formula (I):

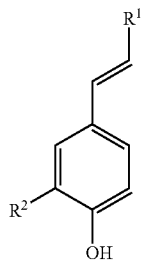

(I)

(wherein $R^1$ represents hydrogen or carboxy, and $R^2$ represents hydrogen or lower alkoxy). The lower alkyl moiety of the above lower alkoxy includes straight-chain or branched alkyl having 1 to 6 carbon atoms, such as methyl, ethyl, propyl, isopropyl, butyl, pentyl and hexyl. In the polymer of compounds represented by general formula (I), the constituent compounds may be the same or different.

The polymers of phenol compounds having a styrene structure include dimers, trimers, tetramers and pentamers of phenol compounds having a styrene structure. Preferred are dimers. More preferred are those represented by the following formulae (II) to (VII):

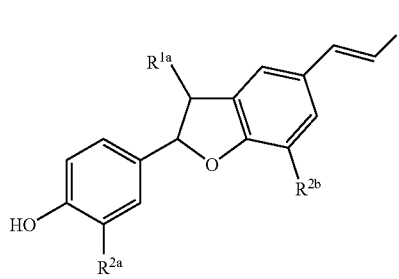

(II)

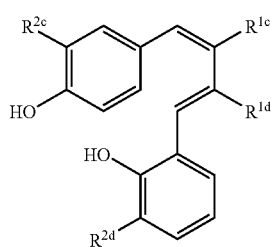

(III)

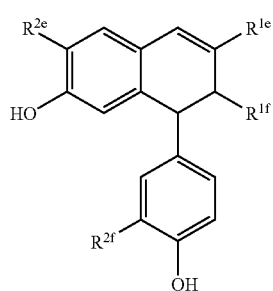

(IV)

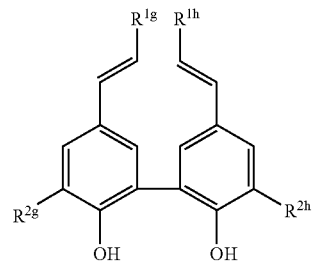

(V)

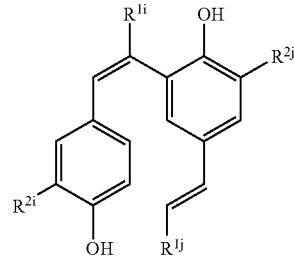

(VI)

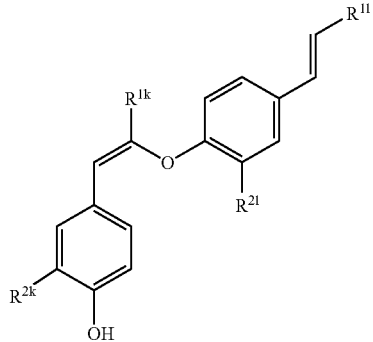

(VII)

wherein $R^{1a}$, $R^{1b}$, $R^{1c}$, $R^{1d}$, $R^{1e}$, $R^{1f}$, $R^{1g}$, $R^{1h}$, $R^{1i}$, $R^{1j}$, $R^{1k}$ and $R^{1l}$, which may be the same or different, each represents hydrogen or carboxy, and $R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$ and $R^{2l}$, which may be the same or different, each represents hydrogen or lower alkoxy). Particularly preferred is 2,3-dihydro-2-(4-hydroxy-3-methoxyphenyl)-7-methoxy-5-vinylbenzofuran (VGD).

Method of obtaining Phenol Compounds Having a Styrene Structure

The phenol compounds having a styrene structure can be synthesized according to known methods. For example, 4-vinylphenol can be obtained by reduction, dehydration and hydrolysis of 4-acetoxyacetophenone. Ferulic acid can be obtained by subjecting 4-hydroxy-3-methoxybenzaldehyde and malonic acid to condensation decarboxylation in pyridine in the presence of piperidine. p-Coumaric acid can be obtained from p-aminocinnamic acid via diazonium salt, or from p-oxybenzaldehyde by the Perkin reaction. 4-Vinylguaiacol can be obtained by preparing 4-acetoxy-3-methoxycinnamic acid from vanillin using acetic anhydride or sodium acetate, followed by hydrolysis and decarboxylation using quinoline.

Some phenol compounds having a styrene structure, e.g. ferulic acid, are also commercially available.

4-Vinylguaiacol, ferulic acid, etc. can also be produced from natural products including food materials.

The methods of producing these phenol compounds from natural products are described below.

Method of Producing Ferulic Acid

Ferulic acid can be obtained by decomposing ferulic acid ester existing in fibrous substances such as arabinoxylan and pectin, which are one of the cell wall components of plants, in the presence of ferulic acid esterase in the usual way. Examples of plants known to contain ferulic acid or ferulic acid ester are cereals (e.g. rice, wheat, barley and buckwheat), potatoes (e.g. potatoes and sweet potatoes), fruits (e.g. grapes, apples and citrus fruits) and vegetables.

Ferulic acid can also be obtained by treating the above plants with fibrous hydrolases such as xylanase, arabinase, cellulase, pectinase and hemicellulase in the usual way.

Further, ferulic acid can be obtained, for example, by decomposing lignin in wood by ordinary methods such as thermal decomposition, ethanol decomposition and use of hydrolases (e.g. ligninase, manganese peroxidase and laccase).

Method of Producing 4-vinylguaiacol

4-Vinylguaiacol can be obtained by treating ferulic acid in the presence of ferulic acid decarboxylase in the usual way. Useful enzyme sources of ferulic acid decarboxylase include not only the enzyme itself, but also cells of filamentous fungi, yeast, etc. having the enzyme activity and crude enzyme extracted from such cells by appropriate means [Appl. Environ. Microbiol., 59(7), 2244 (1993)]. Preferred yeast strains are those having the enzyme activity of 0.5 unit/g (unit is defined in the explanation of Examples hereinbelow) (wet cell weight) or more. Examples of such yeast strains are Saccharomyces cerevisiae IFO 2260, IFO 1953 and IFO 0233 and Dia Yeast (trademark for pressed yeast produced by Kyowa Hakko Kogyo Co., Ltd.).

(1) Method of Producing the Polymer of Phenol Compounds Having a Styrene Structure The method of producing the polymer of phenol compounds having a styrene structure is described below.

The conversion of phenol compounds having styrene structure into the polymer is carried out, for example, by maturing at 10 to 80° C. in a solvent (e.g. a solvent containing ethanol) in the presence of oxygen. For instance, the conversion of 5 ppm 4-vinylguaiacol into VGD is preferably carried out by maturing at 25° C. for 6 months or more, at 37° C. for 4 months or more, or at 60° C. for 20 days or more.

It is preferred to make aeration or blow oxygen into the reaction system in view of reduction in reaction time.

The above conversion reaction can be accelerated under irradiation with light, and further accelerated in the presence of a photosensitizer.

When the reaction is carried out under irradiation with light in the presence of a photosensitizer, the intensity and time of irradiation suitable for the conversion at 5 to 80° C., preferably 10 to 30° C., are selected. For instance, the conversion of 1 liter of a solution containing 5 ppm 4-vinylguaiacol into VGD is preferably carried out by treatment at 20° C. under a fluorescent light of 20 to 40 W for 1 to 3 days, or at 30° C. under a fluorescent light of 20 to 40 W for 0.5 to 2 days.

Preferred light sources are those mainly emitting light with wavelengths in the range of 240 to 500 nm. Examples of such light sources are sunlight, a fluorescent light, an incandescent lamp, a black light lamp, a sterilization lamp and an insect-drawing lamp, which may be used alone or in combination. Particularly, a black light lamp, a sterilization lamp and an insect-drawing lamp are preferred in respect of energy efficiency.

Hydroxymethylfurfural and riboflavin are able to shown as an example of photosensitizer. The conversion rate varies according to the combination of photosensitizer and light source. Preferred combinations are ultraviolet light and hydroxymethylfurfural, riboflavin, etc., and visible light and riboflavin, etc. If a fermentation liquor to be irradiated with light contains riboflavin, whether it is contained in raw materials or formed by fermentation, it is not necessary to add a photosensitizer. The concentration of the photosensitizer is preferably 1 ppb or more, more preferably 10 to 5000 ppb.

The above conversion reaction can also be carried out in the presence of an enzyme capable of converting the phenol compounds having a styrene structure into the polymer.

Useful enzyme sources of such enzymes (e.g. peroxidase) include a peroxidase reagent produced by ICN Biomedicals Inc. and a crude enzyme solution of peroxidase extracted from horseradish with water.

Recovery of the polymer (hereinafter the polymer of phenol compounds having a styrene structure is sometimes referred to merely as the polymer) from the reaction mixture is carried out, for example, by using a nonionic porous resin such as Diaion HP 20 (Mitsubishi Chemical Corporation) (the "nonionic porous resin" as used herein means a resin which does not have a functional group such as an ion-exchange group and adsorbs various organic substances with the van der Waals force). The nonionic porous resin is charged into a column and is equilibrated with 5 to 30% aqueous ethanol or methanol. The reaction mixture is passed through the column to adsorb the polymer on the resin, followed by elution of the polymer with alcohol. If necessary, the elute is dried under reduced pressure to obtain the desired product as a powder.

(2) Method of Removing Off-flavor from Foods

In accordance with the present invention, off-flavor in foods can be reduced or completely removed by causing the polymer of phenol compounds having a styrene structure and/or the reaction mixture comprising the polymer of phenol compounds having a styrene structure obtained by the above method to be present in the foods, for example, by addition of the polymer to the foods.

In this method, not only the polymer in a pure form but also a substance containing the polymer can be employed. For example, the use of the reaction mixture described above and also a crude purified form of the reaction mixture can be employed. For the use of the deodorizer or seasoning of the present invention described below in removal of off-flavor from foods is included within the scope of the method of removing off-flavor from foods.

In the method of removing off-flavor from foods according to the present invention, it is preferred to cause the polymer to be present in the foods at a concentration of 0.5 ppb or more.

(3) Deodorizer

The deodorizer of the present invention is effective for the deodorization of off-flavors in foods such as the fishy smell of seafood, the fleshy smell of meat and the grassy smell of soybean, body odors such as odor caused by maturation and the smell of armpit, etc.

The deodorizer of the present invention can be obtained by mixing the polymer of phenol compounds having a styrene structure with an appropriate solvent (e.g. water, ethanol, and a mixture thereof) or powder (an excipient for the use for foods, e.g. starch, dextrin and lactose, or an excipient for the use as cosmetics, e.g. talc). The solution of the polymer in ethanol or the like, which is obtained in the step of purification from the reaction mixture in the process for producing the polymer, and/or the reaction mixture itself, as such, can also be used as the deodorizer of the present invention. The polymer of phenol compounds having a styrene structure can be obtained by the process described in (1) above or processes similar thereto.

The deodorizer of the present invention may comprise various ingredients according to the use and purpose, in addition to the polymer of phenol compounds having a styrene structure. When the deodorizer is used for the deodorization of foods, it may be, for example, added to foods in the form of a mixture with ethanol, or used as the seasoning of the present invention described below.

When applied to foods, the deodorizer of the present invention may be added in the form of a solution containing the polymer in 1 to 80%, preferably 5 to 30% aqueous ethanol, preferably at a concentration of 10 ppb or more, more preferably 10 ppb to 100 ppm.

For the purpose of removing body odor, the deodorizer of the present invention can be used, for example, as the cosmetic of the present invention described below.

(4) Seasoning

The seasonings of the present invention can be obtained by causing the polymer of phenol compounds having a styrene structure to be present in known seasonings currently used or novel seasonings which will be developed in the future preferably at a concentration of 10 ppb or more, more preferably 10 ppb to 100 ppm. Specifically, the seasonings of the present invention can be obtained by adding the polymer of phenol compounds having a styrene structure to a seasoning as a final product or to materials in any of the steps in a process for producing a seasoning, or by causing phenol compounds having a styrene structure to be present in any of the steps in a process for producing a seasoning, and conducting an oxidation reaction of the phenol compounds in the presence of oxygen during or after the completion of the process. The polymer of phenol compounds having a styrene structure can be obtained by the process described in (1) above or processes similar thereto. The process for conducting an oxidation reaction of the phenol compounds in the presence of oxygen during or after the completion of the process is described in detail in the description of fermented seasoning below.

The preferred seasonings according to the present invention are those containing at least one member of amino acids (e.g. glutamic acid, aspartic acid, alanine, arginine, leucine, tyrosine and glycine), organic acids (e.g. succinic acid, lactic acid, malic acid, citric acid and acetic acid), alcohols (e.g. ethanol, 1-propanol, 2-methylpropanol and isoamyl alcohol), saccharides (e.g. glucose, fructose, sucrose and maltose) and esters (e.g. isoamyl acetate and ethyl caproate). The seasonings of the present invention may be in the form of liquors (e.g. sake, shochu, whiskey and brandy), fermented seasonings, extract seasonings, etc.

Extract Seasoning

The extract seasonings of the present invention are seasonings containing stocks obtained by boiling or smothering meat, marine products, vegetables, etc. or concentrates of the stocks among the seasonings of the present invention described above. Such seasonings include meat extract seasonings, marine product extract seasonings and vegetable extract seasonings. The meat extract seasonings are produced mainly from meat or bones of cattle, pigs, fowls, etc., the marine product extract seasonings are produced mainly from marine products (e.g. bonitos, mackerels, tuna, sardines, croakers, pike congers, thread sea bream, scallops, short-necked clams, oysters, krills and crabs) or dried products thereof, and vegetable extract seasonings are produced mainly from vegetables (e.g. onion, garlic, carrots, Chinese cabbages, cabbages, shiitake mushrooms and tangleweed) or dried products thereof, according to conventional methods.

The extract seasonings of the present invention can be produced in the following manner. An extract material (e.g. dried bonito) is subjected to extraction with a solution containing the polymer of phenol compounds having a styrene structure in ethanol, water, or a mixture thereof (a preferred example is the cooking liquor of the present invention described below) at 5 to 120° C., preferably 20 to 80° C. for 1 to 10 hours, followed by solid-liquid separation to obtain the supernatant as an extract. The obtained extract is concentrated by heating or freezing, by use of membrane, or under reduced pressure, as may be required, whereby the extract seasonings of the present invention are obtained as concentrates.

Fermented Seasoning

The fermented seasonings of the present invention are seasonings produced by utilizing the fermentation by microorganisms or the like among the seasonings of the present invention described above. These seasonings may take various forms such as vinegar, cooking liquor, sake, wine, mirin, soy sauce and miso.

The fermented seasonings of the present invention can be obtained by adding the polymer of phenol compounds having a styrene structure to a fermented seasoning as a final product or to materials in any of the steps in a process for producing a fermented seasoning. However, they are preferably produced by conducting an oxidation reaction of the phenol compounds in the presence of oxygen during or after the completion of the production process for producing a fermented seasoning.

Production of the fermented seasonings of the present invention comprising conducting an oxidation reaction of the phenol compounds in the presence of oxygen during or after the completion of the process for producing a fermented seasoning is exemplified by a process which comprises forming 4-vinylguaiacol during the production process, and after the completion of the production process, converting 4-vinylguaiacol in the obtained fermented seasoning into VGD. This process is explained below referring to the production of a cooking liquor.

As the first step, cereals such as rice (usually containing ferulic acid or ester thereof) as a raw material are liquefied and saccharified using a filamentous fungus such as rice koji. In this step, liquefying enzyme such as α-amylase and saccharifying enzyme such as glucoamylase may be added if necessary. Then, yeast is added to cause fermentation and the obtained fermentation liquor (moromi) is filtered to obtain a cooking liquor as the filtrate. The filamentous fungus used above has also fibrous hydrolase activity and ferulic acid esterase activity and contributes to decomposition of fibers in cereals and liberation of ferulic acid.

In the above step, ferulic acid is formed from cereals in the presence of xylanase together with glucoamylase. The formed ferulic acid is converted into 4-vinylguaiacol by ferulic acid decarboxylase contained in specific yeasts such as those mentioned above in the method of producing 4-vinylguaiacol. The resultant 4-vinylguaiacol is contained in the produced cooking liquor. Filamentous fungi is also utilized in this step in place of yeast fungi in order to use the same enzyme activity, ferulic acid decarboxylase. When ferulic acid decarboxylase contained in filamentous fungi is used, the addition of yeast mentioned above is not necessary.

As the next step, the cooking liquor containing 4-vinylguaiacol is subjected to reaction for converting 4-vinylguaiacol into a polymer such as VGD, whereby the cooking liquor of the present invention containing VGD is obtained. The reaction for converting 4-vinylguaiacol into the polymer can be carried out by the process described in (1) above or processes similar thereto.

The polymer may also be formed during the process for producing a fermented seasoning by adding or forming the phenol compounds having a styrene structure at an appropriate time during the production process and carrying out reaction for converting the phenol compounds into the polymer in the same manner as above at an appropriate time during the production process.

(5) Cosmetic

The cosmetics of the present invention are formulated to contain the polymer of phenol compounds having a styrene structure preferably at a concentration of 10 ppb or more, more preferably 10 ppb to 1 ppm, based on the total weight of the product. The polymer of phenol compounds having a styrene structure and/or the reaction mixture containing the polymer of phenol compounds having a styrene structure can be obtained by the process for producing the polymer described above or processes similar thereto.

The cosmetics of the present invention may further comprise cosmetic bases such as pigments, perfumes, preservatives, surfactants, antioxidants and ultraviolet absorbents, as may be required. The cosmetics can be prepared, for example, according to the methods described in "The development manual of preparations for percutaneous application" 1st ed., Mitsuo Matsumoto ed., [Seishi Shoin (1985)].

Examples of the pigments include tar pigments, iron oxide, titanium oxide and zinc oxide. Examples of the perfumes include animal perfumes such as musk, plant perfumes such as peppermint oil, lemon oil and rose oil, and synthetic perfumes such as benzyl alcohol and anisole. Examples of the preservatives include paraben, methylparaben, ethyl p-oxybenzoate and butyl p-oxybenzoate. Examples of the surfactants include anionic surfactants such as sodium cetyl sulfate, nonionic surfactants such as polyoxyethylene alkyl ether, polyoxyethylene fatty acid ester, polyoxyethylene polyhydric alcohol fatty acid ester, fatty acid ester hardened castor oil, polyhydric alcohol fatty acid ester and polyglycerin fatty acid ester, cationic surfactants such as tetraalkylammonium salt, and amphoteric surfactants such as betaine surfactants, sulfobetaine surfactants, sulfoamino acid surfactants and sodium N-stearoyl-L-glutamate. An example of the antioxidant is dibutylhydroxytoluene. Examples of the ultraviolet absorbents include 2-ethylhexyl p-methoxycinnamate and 4-tert-butyl-4'-methoxydibenzoylmethane.

The cosmetics may take various forms such as cream, emulsion, lotion, essence, enriched lotion and pack. In the case of emulsion, for example, the cosmetic can be produced by a conventional method, that is, by emulsifying an oil phase and a water phase respectively heated and then cooling the resultant emulsion.

The cosmetics of the present invention are effective for the removal of body odor, etc.

(6) Antioxidant

The antioxidant of the present invention contains the polymer of phenol compounds having a styrene structure preferably at a concentration of 10 ppb or more, more preferably 10 ppb to 100 ppm.

The antioxidant of the present invention can be obtained by mixing the polymer of phenol compounds having a styrene structure with an appropriate solvent (e.g. water, ethanol, and a mixture thereof) or powder [e.g. those mentioned in the explanation of powder in (3)]. The solution of the polymer in ethanol or the like which is obtained in the step of purification from the reaction mixture in the process for producing the polymer, as such, can also be used as the antioxidant of the present invention. The polymer of phenol compounds having a styrene structure can be obtained by the method of producing the polymer described above or processes similar thereto.

The antioxidant of the present invention can be used, for example, by adding it to foods, seasonings, cosmetics, etc. as final products or to materials during the processes for producing them, or by adding it to foods during cooking.

The antioxidant of the present invention is useful in preventing oxidation of foods, seasonings, cosmetics, etc. For example, it is useful in preventing oxidation of linoleic acid in foods.

(7) Method of Producing a Deodorized Food Which Comprises Cooking a Food Using the Above Deodorizer and a Food Obtained by this Method The method of producing a deodorized food which comprises cooking a food using the above deodorizer can be carried out, for example, by using the deodorizer described in (3) above in cooking seafood, meat or vegetables (e.g. soybean) preferably in such an amount that the concentration of the polymer of phenol compounds having a styrene structure in the food becomes 0.5 ppb or more. The foods of the present invention which can be obtained by this method are desirable in that they are freed of off-flavor.

(8) Method of Deodorizing a Food Which Comprises Cooking the Food Using the Above Deodorizer The method of deodorizing a food which comprises cooking the food using the above deodorizer can be carried out, for example, by using the deodorizer described in (3) above in cooking seafood, meat or vegetables (e.g. soybean) preferably in such an amount that the concentration of the polymer of phenol compounds having a styrene structure in the food becomes 0.5 ppb or more.

Certain embodiments of the present invention are illustrated in the following examples.

In the following examples, high performance liquid chromatography (HPLC) was carried out under the following conditions.

Column: Inertsil ODS—24.6×250 mm (GL Sciences)
Detector: OD 280 nm

The definitions of enzyme activities as used in the following examples are as follows.

Ferulic Acid Decarboxylase Activity

To 0.9 ml of a culture of test yeast obtained by culturing the yeast in YPD medium at 30° C. overnight with shaking was added 0.1 ml of an aqueous solution containing 1 g/liter ferulic acid (Ichimaru Falcos), and the mixture was allowed to stand at 25° C. The amount of 4-vinylguaiacol in the supernatant of the resultant reaction mixture was determined by HPLC. One unit of the enzyme activity was defined as that amount of the enzyme which forms 1 ppm of 4-vinylguiaicol per hour.

Xylanase Activity

Xylan derived from oats (100 mg, Nacalai Chemicals) was dissolved in 9.0 ml of 50 mol/liter acetate buffer (pH 4.5), followed by addition of 1.0 ml of a test enzyme solution. The mixture was subjected to reaction at 52° C. with stirring, and the change in reducing sugar equivalent in the reaction mixture was determined by the dinitrosalicylic acid reaction. One unit of the enzyme activity was defined as that amount of the enzyme which liberates 1 µmol of reducing sugar equivalent from xylan in one minute.

Determination of the Phenol Compounds

In the following examples, analysis of the phenol compounds having a styrene structure was carried out in the following manner.

A test substance was analyzed by HPLC in the following manner. In the analysis of VGD, a sample was concentrated to make a test solution. The sample (50 ml) was passed through a $C_{18}$ cartridge for HPLC pretreatment and eluted with 0.8 ml of acetonitrile. The eluate was brought to a volume of 1.0 ml and then analyzed under the above conditions.

Fractionation Conditions in HPLC

Mobile phase: solution A: 20 mmol/liter aqueous solution of sodium acetate
solution B: acetonitrile
Elution was carried out with linear gradient of solution B/solution A (volume ratio) of 30 to 80%/25 minutes.
Column temperature: 40° C.
Flow rate: 1.0 ml/minute Seven Points Scoring and Test of Significance In the following examples, the term "seven points scoring" refers to a method of evaluating a subject with respect to the strength of fishy smell by giving the subject scores of one point (weak) to seven points (strong). Student t-test was made as to the significance of difference. The symbol n refers to the number of persons.

EXAMPLE 1

Eight hundred milliliters of 7.75% aqueous ethanol containing 50 ppm 4-vinylguaiacol (4-VG) and 41.6 ppm hydroxymethylfurfural was irradiated with ultraviolet light for 40 minutes. The resultant reaction mixture was passed through Diaion HP 20 (trademark, Mitsubishi Chemical Corporation) equilibrated with 7.75% aqueous ethanol, followed by washing with 80% aqueous methanol. A fraction eluted with 8 ml of methanol (fraction A) was obtained as a crude product.

Separately, 20 liters of 7.75% aqueous ethanol containing 50 ppm 4-vinylguaiacol and 0.5 ppm riboflavin was kept in a thermostat with fluorescent illumination at a reaction temperature of 25° C. for 24 hours. The resultant reaction mixture was passed through Diaion HP 20 (trademark, Mitsubishi Chemical Corporation) equilibrated with 7.75% aqueous ethanol, followed by washing with 80% aqueous methanol. A fraction eluted with 200 ml of methanol (fraction B) was obtained as a crude product.

The fractions obtained above were concentrated 10-fold under reduced pressure and then fractionated by $C_{18}$ HPLC, whereby a purified VGD fraction (fraction C) was obtained for each of the above fractions. Identification of the obtained VGD was carried out.

The fractionation conditions in HPLC and the result of identification of VGD are shown below.

Fractionation Conditions in HPLC

Mobile phase: 20 mmol/liter aqueous solution of sodium acetate/acetonitrile=45/55
Column temperature: 40° C.
Flow rate: 1.0 ml/minute Physical Properties of VGD FAB mass spectrum:
Positive mode: m/z 299 (M+H)+
Negative mode: m/z 297 (M−H)−
$^1$H-NMR (400 MHz, CD$_3$OD); [δ ppm (integration, multiplicity, coupling constant J (Hz)]; 6.98 (1H, d, 2.0), 6.92 (1H, br.s), 6.91 (1H, br.s), 6.84 (1H, dd, 8.1, 2.0), 6.78 (1H, d, 8.1), 6.64 (1H, dd, 17.6, 11.0), 5.69 (1H, t, 8.9), 5.60 (1H, dd, 17.6, 1.1), 5.06 (1H, dd, 11.0, 1.1), 3.86 (3H, s), 3.82 (3H, s), 3.55 (1H, dd, 15.6, 9.3), 3.16 (1H, dd, 15.6, 8.5)
$^{13}$C-NMR (100 MHZ, CD$_3$OD); δ ppm (multiplicity); 149.1 (s), 149.1 (s), 147.7 (s), 145.4 (s), 138.1 (d), 134.5 (s), 133.2(s), 129.7 (s), 120.0 (d), 116.4 (d), 116.2 (d), 111.4 (d), 111.4 (t), 110.7 (d), 86.7 (d), 56.7 (q), 56.4 (q), 39.4 (t)

EXAMPLE 2

Twenty liters of 7.75% aqueous ethanol containing 50 ppm 4-vinylguaiacol and 0.5 ppm riboflavin was kept in a thermostat with fluorescent illumination at a reaction temperature of 25° C. for 24 hours. The resultant reaction mixture was passed through Diaion HP 20 (trademark, Mitsubishi Chemical Corporation) equilibrated with 7.75% aqueous ethanol. After washing with 80% aqueous ethanol, elution was carried out with 200 ml of ethanol to obtain a deodorizer of the present invention. The VGD concentration in this deodorizer was 40.4 ppm.

EXAMPLE 3

Two mixtures were prepared, each consisting of 100 g of onion, 15 g of carrot, 15 g of Welsh onion, 10 g of parsley, 0.5 g of whole pepper, a laurel leaf, 2.5 g of salt, 700 ml of water and 250 g of bony parts of sea bream. To one of the mixtures was added 100 ml of the deodorizer of the present invention obtained in Example 2 (VGD concentration: 40.4 ppm) and to the other (control) was added 100 ml of ethanol. Each of the mixtures was boiled for 20 minutes and then filtered through cloth. The obtained soup was kept at 60° C. and evaluated by seven points scoring with respect to the strength of fishy smell perceived when the lid of the vessel was taken off. The results are shown in Table 1. The soup prepared with addition of VGD of the present invention had a significantly reduced fishy smell, compared with the control.

TABLE 1

|  | VGD-treated soup | Control |
| --- | --- | --- |
| Average score | 2.75* | 4.00 |
| Standard deviation | 0.46 | 0.76 |

*n = 8
*P < 0.01

EXAMPLE 4

To 2.0 liters of water were added 370 g of rice koji, 1.5 g of yeast (Dia Yeast; trademark, Kyowa Hakko Kogyo Co., Ltd.) and 7 g of lactic acid, followed by fermentation at 20° C. for 2 days to obtain a yeast culture (first stage fermentation). To 1.3 liter of water were added 660 g of rice and 2 g of Spitase CP-40G (trademark for α-amylase preparation produced by Nagase Seikagaku Kogyo Co., Ltd., 400000 units/g), and the mixture was liquefied by heating at 90° C.

for 30 minutes and then cooled to 50° C. To the resultant mixture were added 2 g of Sumizyme 3000 (trademark for glucoamylase produced by Shinnihon Kagaku Co., Ltd., 3000 units/g) and 2 g of Sumizyme AC (trademark for hemicellulase produced by Shinnihon Kagaku Co., Ltd., 6400 units/g), followed by reaction at 50° C. for 16 hours to obtain a saccahrified rice liquor. This saccharified rice liquor and 370 g of rice koji were added to the yeast culture, followed by fermentation at 20° C. for 2 days (second stage fermentation).

To 4.4 liters of water were added 1800 g of rice and 7 g of Spitase CP-40G, and the mixture was liquefied by heating at 90° C. for 30 minutes and then cooled to 50° C. To the resultant mixture were added 7 g of Sumizyme 3000 and 7 g of Sumizyme AC, followed by reaction at 50° C. for 16 hours to obtain a saccahrified rice liquor. This saccharified rice liquor was added to the fermentation liquor obtained by the second stage fermentation, followed by fermentation at 20° C. for 7 days (third stage fermentation). The obtained fermentation product was filtered and the filtrate (10 liter) was pasteurized (hereinafter the filtrate prepared in this manner is referred to as moromi).

The amount of 4-vinylguaiacol formed in the fermentation process was 2.1 ppm at the start of the third stage fermentation and 5.1 ppm after 7 days of fermentation.

The moromi obtained above (containing 5 ppm 4-vinylguaiacol) was kept in a thermostat with fluorescent illumination at 25° C. for 24 hours to obtain a cooking liquor of the present invention. The cooking liquor contained 0.1 ppm 4-vinylguaiacol and 67 ppb VGD.

EXAMPLE 5

To 1 liter of the moromi prepared in Example 4 was added 1.2 g of a peroxidase reagent (81.8 units/mg, ICN Biomedicals Inc.), followed by reaction at 25° C. for 48 hours to obtain a cooking liquor of the present invention. The cooking liquor contained 0.2 ppm 4-vinylguaiacol and 66 ppb VGD.

EXAMPLE 6

Commercial materials for oden (Japanese hotchpotch) with soup were cooked using the cooking liquor of the present invention obtained in Example 4 in an amount of 10 wt % based on the soup. The cooked oden was evaluated by seven points scoring with respect to the strength of fishy smell perceived when the lid of the pot was taken off. As a control, the same procedure as above was repeated except for the use of a commercial cooking liquor instead of the cooking liquor of the present invention. The results are shown in Table 2. The cooking liquor of the present invention significantly reduced fishy smell, compared with the commercial one.

TABLE 2

|  | Cooking liquor of the invention | Commercial cooking liquor |
| --- | --- | --- |
| Average score | 3.00* | 4.50 |
| Standard deviation | 1.30 | 0.70 |

*n = 10
*P < 0.05

EXAMPLE 7

Two mixtures were prepared, each consisting of 100 g of onion, 15 g of carrot, 15 g of Welsh onion, 10 g of parsley, 0.5 g of whole pepper, a laurel leaf, 2.5 g of salt, 700 ml of water and 250 g of bony parts of sea bream. To one of the mixtures was added 100 ml of the cooking liquor of the present invention obtained in Example 4 and to the other was added 100 ml of a commercial cooking liquor. Each of the mixtures was boiled for 20 minutes and then filtered through cloth. The obtained soup was kept in a vessel at 60° C. and evaluated by seven points scoring with respect to the strength of fishy smell perceived when the lid of the vessel was taken off. The results are shown in Table 3. The cooking liquor of the present invention significantly reduced fishy smell, compared with the commercial one.

TABLE 3

|  | Cooking liquor of the invention | Commercial cooking liquor |
| --- | --- | --- |
| Average score | 3.47* | 4.93 |
| Standard deviation | 1.06 | 1.16 |

*n = 15
*P < 0.01

EXAMPLE 8

To 350 g of well washed short-necked clams with shells was added 50 ml of the cooking liquor of the present invention obtained in Example 4. The short-necked clams were brought to the boil on a high flame and then heated on a low flame for one minute. The thus cooked short-necked clams were kept at 60° C. and evaluated by seven points scoring with respect to the strength of fishy smell perceived when the lid of the vessel was taken off. The same procedure as above was repeated except for the use of a commercial cooking liquor instead of the cooking liquor of the present invention. The results are shown in Table 4. The cooking liquor of the present invention significantly reduced fishy smell, compared with the commercial one.

TABLE 4

|  | Cooking liquor of the invention | Commercial cooking liquor |
| --- | --- | --- |
| Average score | 3.50* | 5.13 |
| Standard deviation | 1.41 | 1.13 |

*n = 7
*P < 0.05

EXAMPLE 9

A mixture of 5 kg of dried bonito, 1 liter of the cooking liquor of the present invention obtained in Example 4, 1.4 liter of 59% denatured alcohol and 7.6 liter of water was kept at 40° C. for 2 hours, followed by solid-liquid separation to obtain bonito extract. The obtained bonito extract was evaluated by seven points scoring with respect to the strength of fishy smell while being kept at 60° C. The same procedure as above was repeated except for the use of a commercial cooking liquor instead of the cooking liquor of the present invention. The results are shown in Table 5. The cooking liquor of the present invention significantly reduced fishy smell, compared with the commercial one.

TABLE 5

|  | Cooking liquor of the invention | Commercial cooking liquor |
| --- | --- | --- |
| Average score | 3.47* | 4.27 |
| Standard deviation | 1.46 | 0.80 |

*n = 15
*P < 0.05

EXAMPLE 10

A mixture was prepared, which consisted of 0.2 g of methyl p-oxybenzoate, 3.0 g of 1,3-butylene glycol, 0.8 g of sodium citrate, 0.1 g of ethylenediaminetetraacetic acid (EDTA) disodium salt, 0.4 g of polyoxyethylene hardened castor oil, 5.0 g of denatured alcohol, 0.05 g of perfume and 0.5 ml of the deodorizer of the present invention obtained in Example 2. The mixture was made up to 100 ml with purified water to obtain a lotion of the present invention. Ten male adults were made the subjects of this experiment. The obtained lotion (1.0 ml) was infiltrated into absorbent cotton and applied to the armpit of each subject, followed by evaluation of the odor of armpit by seven points scoring. The results are shown in Table 6. The lotion of the present invention significantly reduced unpleasant odor of armpit, compared with the control lotion containing no VGD.

TABLE 6

|  | Lotion of the invention | Commercial lotion |
| --- | --- | --- |
| Average score | 3.60* | 4.80 |
| Standard deviation | 1.20 | 1.40 |

*n = 10
*P < 0.05

EXAMPLE 11

Antioxidation test was carried out on an antioxidant of the present invention (VGD solution) according to the method of Tsushida, et al. [J. Jap. Soc. for Food Science and Technology, 41(9), 611 (1994)].

The test solutions were examined for the ability to inhibit autoxidation of linoleic acid based on the inhibition of fading of β-carotene color. In 10 ml of chloroform were respectively dissolved 10 mg of β-carotene, 1 g of linoleic acid and 2 g of Tween 80, and the solutions (0.5 ml, 0.2 ml and 1.0 ml, respectively) were put into a 200-ml Erlenmeyer flask. After the air in the system was substituted by nitrogen, the mixture in the flask was dried and then dissolved in 100 ml of distilled water. The obtained solution (45 ml) was mixed with 4 ml of 0.2 mol/liter phosphate buffer (pH 6.0) to prepare a substrate solution. The substrate solution (2.9 ml) was mixed with 0.1 ml of the cooking liquor of the present invention obtained in Example 4. The mixture was heated in a thermostat at 60° C. and the change in absorbance (OD) at 470 nm was measured. Separately, a solution of 790 ppm VGD in acetonitrile and a commercial sake were respectively added to the substrate solution and the change in OD was measured in the same manner. The rate (%) of OD value measured 24 hours after the start of oxidation of linoleic acid based on the OD value at the start of oxidation is shown in Table 7. Oxidation of linoleic acid was inhibited by the addition of the cooking liquor of the present invention and VGD.

TABLE 7

|  | OD* (%) |
| --- | --- |
| Cooking liquor of the invention | 27.3 |
| Commercial sake | 14.8 |
| VGD (790 ppm) | 36.7 |
| Control | 1.1 |

*Rate of OD value measured 24 hours after the start of oxidation of linoleic acid based on the OD value at the start of oxidation

EXAMPLE 12

The moromi obtained in Example 4 was kept at 60° C. in the dark for 14 days, whereby a cooking liquor of the present invention containing 25 ppb VGD was obtained. The 4 VG concentration in this cooking liquor was 0.01 ppm.

EXAMPLE 13

To 100 ml of water were added 65 g of rice koji, 35 g of steamed rice, 0.1 g of yeast (Dia Yeast; trademark, Kyowa Hakko Kogyo Co., Ltd.) and 1 ml of lactic acid, followed by fermentation at 15° C. for 2 days to obtain a yeast culture (first stage fermentation). To the resultant mixture were added 135 g of steamed rice, 65 g rice koji, 0.8 g of Sumizyme AC (trademark for hemicellulase produced by Shinnihon Kagaku Co., Ltd., 6400 units/g) and 200 ml of water, followed by initial reaction at 15° C. for 2 days. Then, to the resultant mixture were added 235 g of steamed rice, 65 g rice koji and 400 ml of water, followed by intermediate reaction at 15° C. for 2 days. Thereafter, to the resultant mixture were added 330 g of steamed rice, 70 g rice koji and 500 ml of water, followed by final reaction at 15° C. for 19 days. The obtained fermentation product was filtered and the filtrate was pasteurized to obtain moromi. The moromi obtained above was kept in a thermostat with fluorescent illumination at 25° C. for 24 hours to obtain sake. In the above example, the second stage fermentation is composed of intermittent reactions. There is no limit to the number of reactions. It takes three reactions in the above, for example as initial reaction, intermediate reaction and finial reaction. It also be able to take two reaction, for example as initial reaction and final reaction.

What is claimed is:

1. A method of producing liquor, comprising:
   (a) liquefying and saccharifying a rice using a filamentous fungus;
   (b) fermenting resultant matter obtained in (a), using yeast;
   (c) separating liquid by filtering resultant matter from (b); and
   (d) conducting an oxidation reaction of resulting liquid obtained in (c), at a temperature in a range of 10° to 80° C., in the presence of oxygen.

2. The method according to claim 1, wherein the oxidation reaction is carried out under irradiation with light.

3. The method according to claim 2, wherein the oxidation reaction is carried out in the presence of a photosensitizer.

4. The method according to claim 1, wherein the oxidation reaction is carried out by aeration or blowing oxygen into the reaction system.

5. The method according to claim 4, wherein the oxidation reaction is carried out under irradiation with light.

6. The method according to claim 5, wherein the oxidation reaction is carried out in the presence of a photosensitizer.

7. The method according to claim 1, wherein the yeast has ferulic acid decarboxylase activity.

8. The method according to claim 1, wherein the oxidation reaction is carried out in the presence of an enzyme which accelerates the oxidation reaction.

9. The method according to claim 8, wherein the enzyme is peroxidase.

10. The method according to claim 1, wherein said liquor is a cooking liquor.

11. The method according to claim 1, wherein said liquor is sake.

12. The method according to claim 1, wherein said liquid separated by filtering in step (c) includes phenol compounds having a styrene structure, and in conducting said oxidation reaction the phenol compounds are converted into polymers thereof.

13. The method according to claim 12, wherein said phenol compounds having a styrene structure have hydroxyl and vinyl substituents on a benzene ring.

14. The method according to claim 12, wherein said phenol compounds having a styrene structure are compounds represented by formula (I):

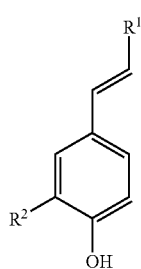

(I)

wherein $R^1$ represents hydrogen or carboxy, and $R^2$ represents hydrogen or lower alkoxy.

15. The method according to claim 14, wherein a lower alkyl moiety of said lower alkoxy has 1 to 6 carbon atoms.

16. A method of producing liquor, comprising:
(a) liquefying and saccharifying a rice using a filamentous fungus;
(b) fermenting resultant matter obtained in (a), using yeast;
(c) separating liquid by filtering resultant matter from (b); and
(d) conducting an oxidation reaction of resulting liquid obtained in (c), at a temperature in a range of 10° to 30° C., in the presence of oxygen.

17. The method according to claim 16, wherein the oxidation reaction is carried out under irradiation with light.

18. The method according to claim 17, wherein the oxidation reaction is carried out in the presence of a photosensitizer.

19. The method according to claim 16, wherein the oxidation reaction is carried out by aeration or blowing oxygen into the reaction system.

20. The method according to claim 19, wherein the oxidation reaction is carried out under irradiation with light.

21. The method according to claim 20, wherein the oxidation reaction is carried out in the presence of a photosensitizer.

22. The method according to claim 16, wherein the yeast has ferulic acid decarboxylase activity.

23. The method according to claim 16, wherein the oxidation reaction is carried out in the presence of an enzyme which accelerates the oxidation reaction.

24. The method according to claim 23, wherein the enzyme is peroxidase.

25. The method according to claim 16, wherein said liquor is a cooking liquor.

26. The method according to claim 16, wherein said liquor is sake.

27. The method according to claim 16, wherein said liquid separated by filtering in step (c) includes phenol compounds having a styrene structure, and in conducting said oxidation reaction the phenol compounds are converted into polymers thereof.

28. The method according to claim 27, wherein said phenol compounds having a styrene structure have hydroxyl and vinyl substituents on a benzene ring.

29. The method according to claim 27, wherein said phenol compounds having a styrene structure are compounds represented by formula (I):

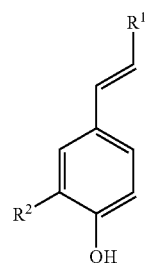

(I)

wherein $R^1$ represents hydrogen or carboxy, and $R^2$ represents hydrogen or lower alkoxy.

30. The method according to claim 29, wherein a lower alkyl moiety of said lower alkoxy has 1 to 6 carbon atoms.

* * * * *